US00PP35127P2

(12) United States Plant Patent
Dirr et al.

(10) Patent No.: US PP35,127 P2
(45) Date of Patent: Apr. 25, 2023

(54) ***HYDRANGEA* PLANT NAMED 'SC-05-20'**

(50) Latin Name: *Hydrangea macrophylla*
Varietal Denomination: SC-05-20

(71) Applicant: Premier Introductions, Inc., Watkinsville, GA (US)

(72) Inventors: Michael Dirr, Bogart, GA (US); Jeff Beasley, Lavonia, GA (US); Mark Griffith, Watkinsville, GA (US)

(73) Assignee: Premier Introductions Inc., Watkinsville, GA (US)

( * ) Notice: Subject to any disclaimer, the term of this patent is extended or adjusted under 35 U.S.C. 154(b) by 0 days.

(21) Appl. No.: 17/894,357

(22) Filed: Aug. 24, 2022

(51) Int. Cl.
*A01H 5/02* (2018.01)
*A01H 6/48* (2018.01)

(52) U.S. Cl.
USPC ..... Plt./250
CPC ..... *A01H 6/48* (2018.05); *A01H 5/02* (2013.01)

(58) Field of Classification Search
USPC ..... Plt./250
CPC ... A01H 5/02; A01H 5/00; A01H 5/12; A01H 6/48
See application file for complete search history.

(56) References Cited

U.S. PATENT DOCUMENTS

PP25,566 P3 * 5/2015 Dirr ..... A01H 5/02 Plt./250

* cited by examiner

*Primary Examiner* — June Hwu
(74) *Attorney, Agent, or Firm* — Cassandra Bright

(57) ABSTRACT

A new and distinct cultivar of *Hydrangea* plant named 'SC-05-20' is disclosed, characterized by glossy dark green foliage color, remontant (reblooming) trait, flowering on old wood and new growth of the season, pink mophead inflorescence in non-aluminium-based media and blue inflorescence in aluminum-based media, and compact, rounded to spreading growth habit. The new variety is a *Hydrangea*, typically produced as an outdoor ornamental plant.

4 Drawing Sheets

Figure 1:
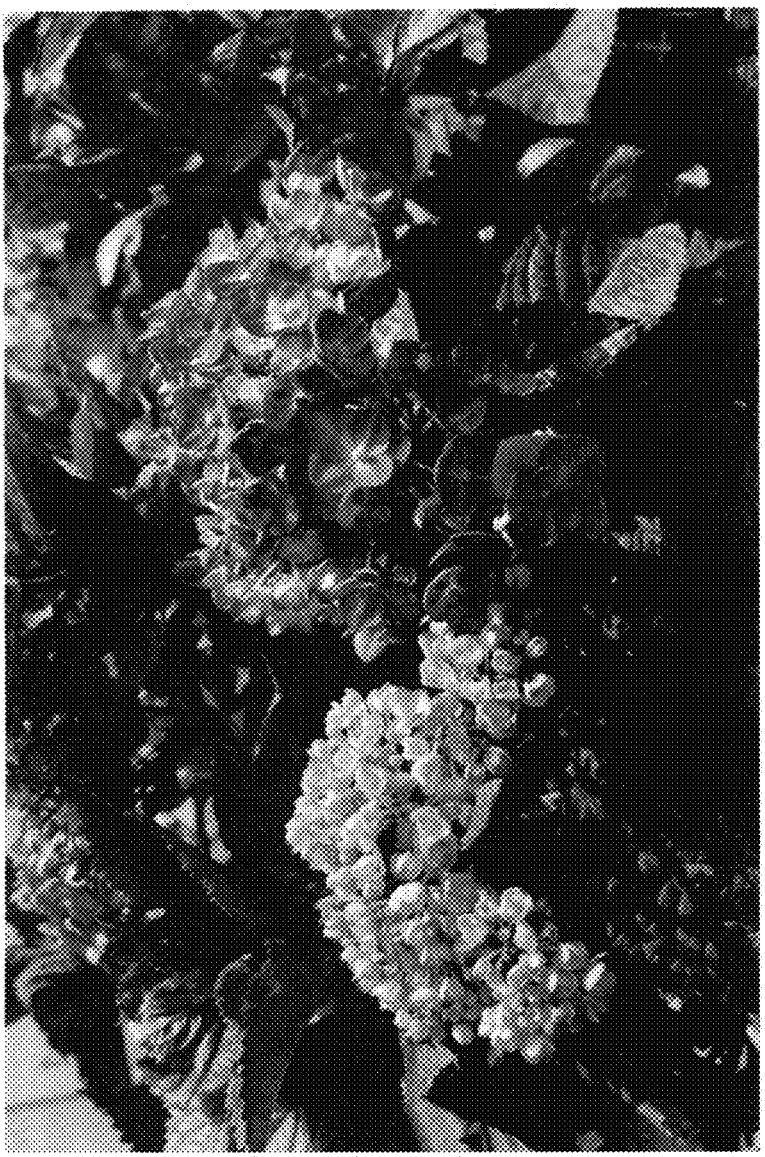

Latin name of the genus and species: *Hydrangea macrophylla.*

Variety denomination: 'SC-05-20'.

BACKGROUND OF THE INVENTION

The present invention relates to a new and distinct cultivar of *Hydrangea macrophylla*, a member of the Hydrangeaceae family, hereinafter referred to by its cultivar name 'SC-05-20'. This cultivar is grown primarily as an ornamental for landscape use and for use as a potted plant. The cultivar originated from an open pollination of *Hydrangea macrophylla* 'Bailmacfive', U.S. Plant Pat. No. 30,359, in Watkinsville, Ga., in 2020, and was selected from the progeny by continued evaluation for growth habit, floral, and foliage characteristics.

'SC-05-20' has been asexually reproduced by softwood cuttings since 2020 in Watkinsville, Ga. The characteristics of the cultivar have been stable and reproduced true to type in successive vegetative generations.

SUMMARY OF THE INVENTION

'SC-05-20' has not been observed under all possible environmental conditions. The phenotype may vary somewhat with changes in light, temperature, soil and rainfall without, however, any variance in genotype.

The following traits have been repeatedly observed and are determined to be the unique characteristics of 'SC-05-20.' These characteristics in combination distinguish 'SC-05-20' as a new and distinct *Hydrangea* cultivar:

1. Glossy dark-green foliage with red veins and petioles.
2. The foliage displays high mildew and *Cercospora* resistances.
3. Remontant (reblooming) trait, flowering on old wood and new growth of the season.
4. Deep pink mophead inflorescence in non-aluminum-based media and blue inflorescence in aluminum-based media.
5. Compact, rounded to spreading growth habit.

PARENT COMPARISON

Plants of the new cultivar *Hydrangea* 'SC-05-20' can be compared to the seed parent variety in most horticultural characteristics, however, plants of 'SC-05-20' differ in the following:

1. 'SC-05-20' is more compact than *Hydrangea macrophylla* 'Bailmacfive'.
2. The stems of 'SC-05-20' are a brighter red than 'Bailmacfive'.
3. The foliage is more resistant to diseases than 'Bailmacfive'.

COMMERCIAL COMPARISON

Plants of the new cultivar *Hydrangea* 'SC-05-20' can be compared to the commercial variety *Hydrangea macrophylla* 'PIIHM-II', U.S. Plant Pat. No. 25,566. Plants of 'SC-05-20' are similar to plants of 'PIIHM-II' in most horticultural characteristics, however, plants of 'SC-05-20' differ in the following:

1. 'PIIHM-II' has longer internodes, a less compact habit, inflorescences that are pink in color or violet-purple depending on the pH levels and aluminum availability of the soil, than that of 'SC-05-20'.

Plants of the new cultivar *Hydrangea* 'SC-05-20' can be compared to the commercial variety *Hydrangea macrophylla* 'Pia', unpatented. Plants of 'SC-05-20' are similar to plants of 'Pia' in most horticultural characteristics, however, plants of 'SC-05-20' differ in the following:

1. 'Pia' is very frost sensitive, and has no rebloom, whereas 'SC-05-20' is more cold hardy.
2. 'Pia has similar inflorescence that are red-pink in color, but 'SC-05-20' reblooms on new wood, whereas 'Pia' does not.

BRIEF DESCRIPTION OF THE PHOTOGRAPHS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Hydrangea*.

FIG. 1: shows 'SC-05-20' plant grown with aluminum. This plant is approximately 12 months old.

Figure 2:
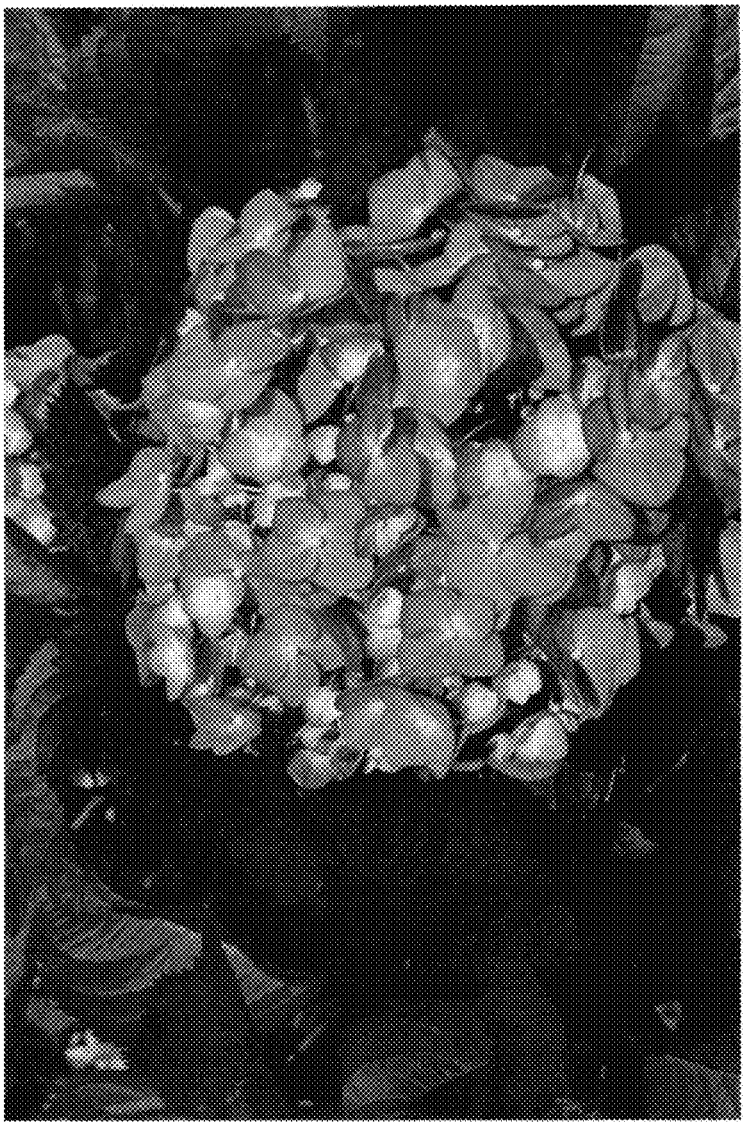

FIG. 2: shows 'SC-05-20' plant grown in absence of aluminum. This plant is approximately 15 months old.

Figure 3:
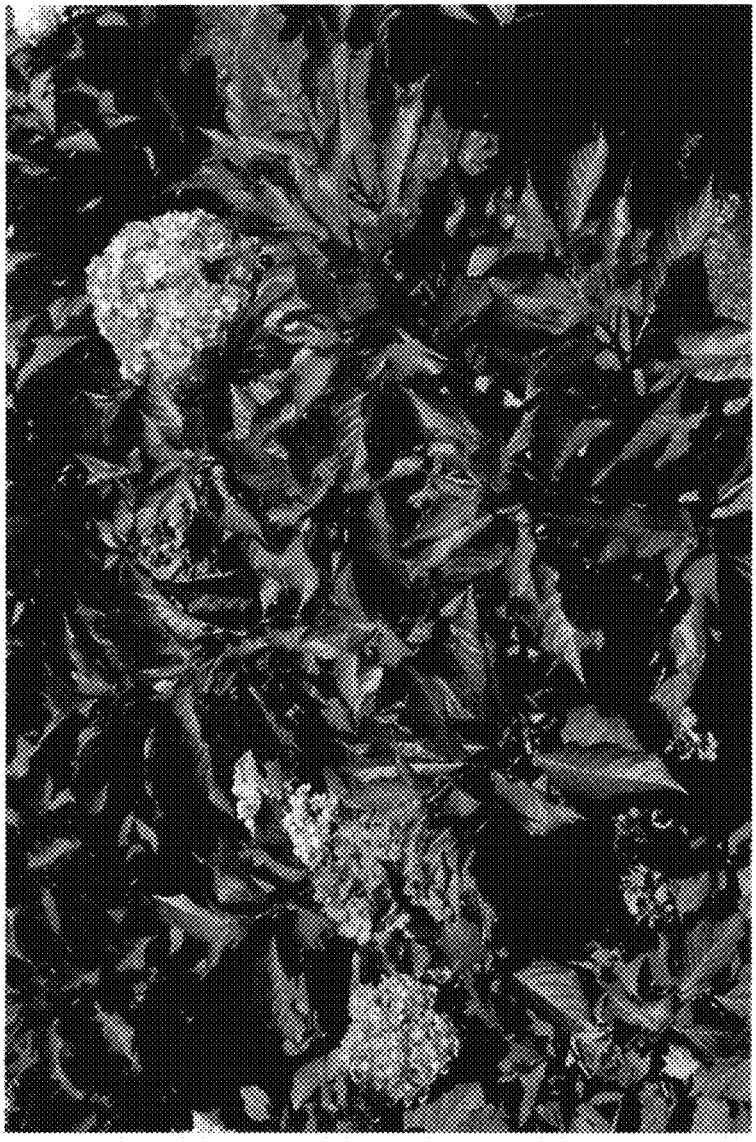

FIG. 3: shows the original 'SC-05-20', with red-stems and glossy dark green foliage. This plant is approximately 16 months old.

Figure 4:
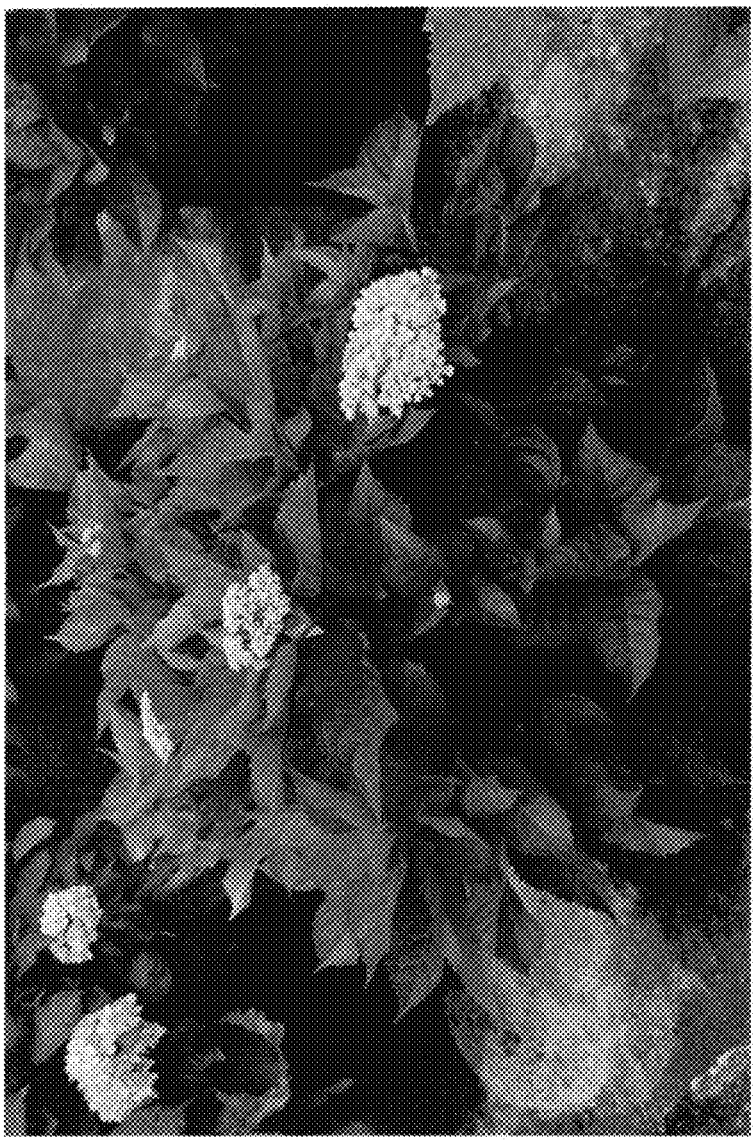

FIG. 4: shows the habit on 'SC-05-20'. This plant is approximately 14 months old.

DETAILED BOTANICAL DESCRIPTION

In the following description, color references are made to The Royal Horticultural Society Colour Chart, 2015 Edition, except where general terms of ordinary dictionary significance are used. Plants used for the description were grown in 3 gallon containers under 50% shade under outdoor conditions in a nursery in Watkinsville, Ga. Plants were about two years old when the description was recorded. Two groups of plants were used for the description to describe the flower colors with and without aluminum. The first group was grown in a medium consisting of composted pine bark, with no aluminum present and a pH of 5.4. The second group was grown in a medium consisting of composted pine bark that was amended with 60 grams of aluminum sulphate and a pH of 5.3. Aluminum only affects flower including sepal, petal, pistil and stamen colors. Therefore, colors with and without aluminum are only specified for floral parts.

Botanical classification: *Hydrangea macrophylla* 'SC-05-20'.

PROPAGATION

Typical method: Vegetatively by stem cuttings.

Root initiation: Approximately 14 days at 32° C.

Time to produce rooted cutting: About 3 months at 32° C. during summer.

Time to produce a finished crop: In a 11.4 L container potted with a 0.041 L liner pot, about 9 months.

Roots: Root description: numerous, fine, fibrous and well-branched. Color: RHS White NN155C.

PLANT

Plant type: Rounded and spreading deciduous shrub.

Height: 56 cm.

Plant spread: 111 cm.

Age of plant described: Approximately 2 years.

Branching characteristics: Freely-branching. Pinching enhances branching.

*Number of lateral branches*.—About 6 per plant.

First year stems:

*Length*.—24 cm.
*Width*.—4 mm.
*Color*.—RHS Red 185A.
*Shape*.—Round.
*Strength*.—Flexible.
*Texture*.—Smooth.

Second year stems:

*Length*.—43 cm.
*Width*.—6 mm or more.
*Color*.—RHS Brown 199C.
*Shape*.—Round.
*Strength*.—Easily broken.
*Texture*.—Woody. Exfoliation begins on second year and older stems, flaky and stringy, the color is RHS Brown 199A.

Stem fasciation: Not present.

Stem lenticels: Only observed on new growth and older growth. Many on new growth, moderate on older growth. Round, about 1 mm in diameter on new growth; about 2 mm in diameter on older growth. Colored near Greyed-Purple 187A.

Vegetative buds:

*Arrangement*.—Opposite.
*Shape*.—Ovoid.
*Length*.—2 mm.
*Width*.—1 mm.
*Color*.—RHS Red 185A.

FOLIAGE

Leaf:

*Arrangement*.—Opposite, simple.
*Shape*.—Ovate.
*Length*.—15 cm.
*Width*.—13 cm.
*Apex*.—Acuminate.
*Base*.—Cuneate.
*Margin*.—Serrate.
*Strength*.—Durable.
*Texture of top surface*.—Glabrous.
*Texture of bottom surface*.—Glaucescent.
*Color*.—Young foliage upper side: RHS Yellow-Green 143B. Young foliage under side: RHS Yellow-Green 147C. Mature foliage upper side: RHS Yellow-Green 141A. Mature foliage, under side: RHS Yellow-Green 144A. Fall foliage: Can be RHS Red-Purple N77A, Yellow-Green 143A, or any combination of these colors.

Venation:
*Type*.—Pinnate.
*Color*.—Young, upper side: RHS Yellow-Green 144A. Young, under side: RHS Red 60A. Mature, upper side: RHS Yellow-Green 144A. Mature, under side: RHS Red 60A.

Petiole:
*Length*.—2 cm.
*Width*.—2.5 mm.
*Color*.—Upper side: RHS Red 185A. Under side: RHS Red 185A.
*Texture*.—Smooth, glabrous. Petiole is grooved on upper side, and crescent-shaped in cross section.

INFLORESCENCE

Natural flowering season: Early summer to first frost in fall. The inflorescence is effective for about 8 weeks.

Inflorescence type: Mophead.
*Height*.—8 cm.
*Diameter*.—14 cm.

Inflorescence shape: Flatted to globular. Becoming less flattened and more globular with maturity.

Fragrance: None.

Bud:
*Bud length*.—6 mm.
*Bud diameter*.—4 mm.
*Bud shape*.—Ovoid.
*Bud color*.—Prior to opening: RHS Yellow-Green 143A. When opening, with aluminum: RHS Purple N80A. When opening, without aluminum: RHS Purplish Red 63B.

Sterile florets:
*Flowers per inflorescence*.—About 300.
*Diameter*.—3.8 cm.
*Density*.—Dense.

Sepals:
*Number per flower*.—4.
*Length*.—2 cm.
*Width*.—1.5 cm.
*Texture*.—Upper side: Smooth. Under side: Smooth.
*Shape*.—Ovoid.
*Tip*.—Obtuse.
*Base*.—Acute.
*Margin*.—Entire.
*Attitude*.—Nearly horizontal.
*Undulation*.—Absent.
*Intensity of overlap*.—Moderate.
*Color*.—When opening, with aluminum: Upper side: RHS Yellow-Green 150D. Under side: RHS Yellow-Green 150D. When opening, without aluminum: Upper side: RHS White 155B flushed Yellow 4D, margins very lightly flushed Red-Purple 62C. Under side: RHS White 155B. At maturity, with aluminum: Upper side: RHS Purple N81A. Under side: RHS Purple N80C. At maturity, without aluminum: Upper side: RHS Purplish Red 67B. Under side: RHS Purplish Red 68C. Aged sepals, with aluminum: Upper side: RHS Light Purple 85C. Under side: RHS Light Purple 85D. Aged sepals, without aluminum: Upper side: RHS Red-Purple 62C flushed Red-Purple 59B. Under side: RHS Red-Purple 62D flushed Red-Purple 59B.

Fertile flowers:
*Flowers per inflorescence*.—About 75.
*Conspicuousness*.—Inconspicuous.

Petals:
*Number per flower*.—5.
*Shape*.—Ovate.
*Tip*.—Acuminate.
*Base*.—Truncate.
*Margin*.—Entire.
*Length*.—3 mm.
*Width*.—1.5 mm.
*Texture*.—Smooth, no pubescence.
*Color*.—With aluminum, upper side: RHS Purple N81A. With aluminum, under side: RHS Purple N81C. Without aluminum, upper side: RHS Purplish Pink 73C. Without aluminum, under side: RHS Purplish Pink N74D.
*Sepal color*.—With aluminum, upper side: RHS Purplish Blue 100C. With aluminum, under side: RHS Purplish Blue 100C. Without aluminum, upper side: RHS Purplish Pink 63C. Without aluminum, under side: RHS Purplish Pink 63C.

Peduncle:
*Length*.—4.5 cm.
*Diameter*.—4 mm.
*Angle*.—Upright.
*Strength*.—Moderately strong and flexible.
*Color*.—RHS Yellow-Green 145C with a hint of Red 185A (with and without aluminum).

Pedicel:
*Length*.—1.2 cm.
*Diameter*.—1 mm.
*Angle*.—45°.
*Strength*.—Moderately strong and flexible.
*Texture*.—Smooth.
*Color*.—With aluminum: RHS Purplish Blue 96A. Without aluminum: RHS Yellow-Green 145C with a hint of Red 185A.

REPRODUCTIVE ORGANS

Stamens:
*Number*.—4 to 5 per flower.
*Filament length*.—3 mm.
*Filament color*.—With aluminum: RHS Purplish Blue 100B. Without aluminum: RHS Purplish Red 63A.

Anthers:
*Length*.—About 1 mm.
*Width*.—0.5 mm.
*Color*.—With aluminum: RHS Purplish Blue 100B. Without aluminum: RHS Purplish Red 63B.
*Pollen amount*.—Moderate.
*Pollen color*.—RHS Yellow-White 155D.

Pistil:
*Number*.—1.
*Length*.—3 mm.
*Width*.—1.5 mm.
*Color*.—With aluminum: RHS Purplish Blue 100B. Without aluminum: RHS Purplish Red 65A.

Stigma:
*Number*.—2 or 3.
*Shape*.—Round.
*Color*.—With aluminum: RHS Purplish Blue 100B. Without aluminum: RHS Purplish Red 62B.
*Style length*.—2 mm.

*Style shape*.—Tubular.

*Style color*.—With aluminum: RHS Purplish Blue 100A. Without aluminum: RHS Purple 85D.

OTHER CHARACTERISTICS

Fruit:

*Number*.—Varies widely.

*Shape*.—Cup-shaped capsule.

*Length*.—3 mm.

*Width*.—2 mm.

*Color*.—During ripening: RHS Purplish Pink 54B. At maturity: Near RHS Brown 200C.

Seeds:

*Number*.—About 50 seeds per capsule.

*Shape*.—Round.

*Length*.—0.5 mm.

*Width*.—0.5 mm.

*Color*.—Near RHS Brown 199B.

Disease resistance: *Hydrangea macrophylla* 'SC-05-20' has high powdery mildew and *Cercospora* resistance.

Drought tolerance and cold tolerance: USDA Hardiness Zone Map (2012): Zones 5-9.

What is claimed is:

1. A new and distinct cultivar of *Hydrangea* plant named 'SC-05-20' as herein illustrated and described.

* * * * *